United States Patent [19]

Hirozawa et al.

[11] Patent Number: 5,419,845
[45] Date of Patent: May 30, 1995

[54] PERFLUORINATED GEMDIPHOSPHONATES AS CORROSION INHIBITORS FOR ANTIFREEZE COOLANTS AND OTHER FUNCTIONAL FLUIDS

[75] Inventors: Stanley T. Hirozawa, Bloomfield Hills; David E. Turcotte; Michael C. Welch, both of Woodhaven; Michael A. Reynolds, Grosse Ile, all of Mich.

[73] Assignee: BASF Corporation, Mt. Olive, N.J.

[21] Appl. No.: 213,343

[22] Filed: Mar. 15, 1994

[51] Int. Cl.$^6$ .................. C09K 5/00; C23F 11/10; C07F 9/02
[52] U.S. Cl. .................. 252/78.5; 106/13; 106/14.12; 106/14.41; 252/70; 252/389.2; 252/289.23; 422/7; 422/15; 558/70; 558/141; 562/8; 568/16
[58] Field of Search .................. 106/14.41, 13, 14.12; 252/70, 78.5, 388, 389.2, 41, 389.23; 558/141, 70; 562/8; 422/7, 15; 568/16

[56] References Cited

U.S. PATENT DOCUMENTS

| | | | |
|---|---|---|---|
| 3,624,188 | 11/1971 | Curry | 558/141 |
| 3,627,842 | 12/1971 | Nicholson | 558/87 |
| 3,855,284 | 12/1974 | Germscheid | 562/22 |
| 3,935,125 | 1/1976 | Jacob | 252/389.22 |
| 4,478,763 | 10/1984 | McKenna | 562/21 |
| 4,613,450 | 9/1986 | Moran et al. | 252/181 |
| 4,707,286 | 11/1987 | Carr | 252/75 |
| 5,000,916 | 3/1991 | Vakasovich et al. | 422/14 |
| 5,043,330 | 8/1991 | Nguyen et al. | 558/161 |
| 5,230,819 | 7/1993 | Hirozawa et al. | 252/78.5 |

Primary Examiner—Anthony Green

[57] ABSTRACT

A coolant or antifreeze composition has one or more glycols or glycol ethers in combination with water, one or more additives, and an effective amount of one or more perfluoro-gem-diphosphonates as corrosion inhibitors.

16 Claims, 4 Drawing Sheets

PERFLUORINATED GEMDIPHOSPHONATES AS CORROSION INHIBITORS FOR ANTIFREEZE COOLANTS AND OTHER FUNCTIONAL FLUIDS

FIELD OF THE INVENTION

The present invention relates to perfluorinated gem-diphosphonates and their use as corrosion inhibitors for metal, and also to functional fluids, especially coolant compositions, and more specifically to coolant compositions comprising one or more perfluorinated gem-diphosphonates.

BACKGROUND OF THE INVENTION

The use of aluminum parts in the automotive industry is now well established. Aluminum radiators are found in many late model passenger cars and other automotive vehicles. Most coolant or antifreeze compositions for use in such radiators and coolant systems contain one or more corrosion inhibitors. These corrosion inhibitors are utilized to prevent the deterioration of the aluminum in contact with the antifreeze.

Presently, perhaps the most cost effective corrosion inhibitor for aluminum is silicate. There are numerous patents and publications directed to the use of silicate as a corrosion inhibitor in coolant compositions. However, silicate is very pH sensitive and has a tendency to gel irreversibly. Thus, there have been many reported instances of deposits "dropping out" of coolants with high silicate levels. Silicate is also alleged to be somewhat aggressive on some foreign-made water pumps.

Several attempts have been made at stabilizing coolant compositions so as to prevent the fall out of gelled deposits. Diphosphonic acid corrosion inhibitors have been proposed for this purpose. For example, 1-hydroxyethylidene-1,1-diphosphonic acid or HEDPA is known in the art as a corrosion inhibitor for mild steel, and is currently available from Monsanto under the trademark DEQUEST (R) 2010. HEDPA may be prepared according to the following reaction:

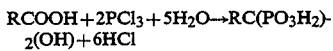

wherein R=the alkyl radical having one carbon atom less than the carboxylic acid used in the above reaction. For HEDPA, R=1. HEDPA has been shown to be extremely aggressive against aluminum.

Other patents also relate to the use of phosphate compounds to prevent corrosion in aluminum and other metal-based systems containing coolant formulations. Carr, U.S. Pat. No. 4,707,286, relates to the use of certain organic phosphonate compounds and certain organic silicon compounds as stabilizers for coolant compositions.

Moran et al., U.S. Pat. No. 4,613,450, discloses corrosion inhibitors for protecting metallic surfaces which come into contact with water. The primary constituent of these corrosion inhibitors are fluorophosphate compounds.

Vukasovich et al., U.S. Pat. No. 5,000,916, is directed to the use of a molybdenum carboxylic compound and the use thereof as a corrosion inhibitor of steel and other metals in cooling water.

Jacob, U.S. Pat. No. 3,935,125, relates to a method and composition for inhibiting corrosion in aqueous systems, the composition including a mixture of amine pyrophosphate, an organophosphonate, and triazole.

According to U.S. Pat. No. 5,230,819, another group of compounds has now been found to be extremely effective in controlling corrosive build-up on aluminum and other metals such as copper, brass, steel and solder. These compounds include 1-hydroxyoctylidene-1,1-diphosphonic acid (HODPA), and 1-hydroxydodecylidene-1,1-diphosphonic acid (HDDPA), and may be derived from the above reaction formula where R=7 and R=11, respectively. Accordingly, preferred starting materials include octanoic and dodecanoic acids, respectively.

What is needed in the art are compounds which can serve as even better corrosion inhibitors than the aforementioned gem-diphosphonates in antifreeze formulations, hydraulic fluids, cutting fluids, and other functional fluids.

Another application of gem-diphosphonates may be in the reduction of friction of metallic parts traversing a fluid medium, e.g., propellers on boats, ships and aircraft, airplane wings and bodies, and the hulls of boats and ships. Another application could be the use of diphosphonates as extreme pressure lubricants, such as in pumps. At present, gem-diphosphonates with hydrocarbon alkyl groups cannot be applied to space craft because hydrocarbons are too fragile at the high temperature of the outer skin of the vessel when it reenters the earth's atmosphere.

Thus, there is also a requirement that the anti-friction and anti-icing properties of gem-diphosphonates be improved as well.

OBJECTS OF THE INVENTION

It is therefore an object of the present invention to provide novel perfluorinated gem-diphosphonate compounds as corrosion inhibitors in functional fluids such as antifreeze.

Another object of the invention is to provide functional fluids such as coolant or antifreeze compositions, hydraulic fluids, and cutting fluids with improved anti-corrosive properties.

It is also an object of the present invention to provide a coolant composition which includes an effective amount of one or more perfluorinated gem-diphosphonates as corrosion inhibitors.

A further object of the present invention is to provide a method of inhibiting corrosion utilizing one or more of the compounds selected from the group of perfluorinated gem-diphosphonates.

Yet another object of the invention is to provide a glycol ether based antifreeze formulation which comprises an effective amount of perfluorinated gem-diphosphonates as corrosion inhibitors.

Another object would include providing perfluorinated gem-diphosphonates for use in anti-friction and deicing applications, such as for ships, aircraft and spacecraft.

SUMMARY OF THE INVENTION

The present invention provides for the use of per fluorinated gem-diphosphonates as corrosion inhibitors in functional fluids, especially coolant compositions for metals, especially aluminum. The terms "perfluorinated" and "perfluoro" are used interchangeably herein.

These and other objects of the invention are achieved through a functional fluid composition effective in inhibiting corrosion which comprises one or more glycols or glycol ethers and an effective amount of one or more perfluorinated gem-diphosphonates. In one preferred embodiment of the invention, the glycol utilized as part of the functional fluid is ethylene glycol.

Also included as part of the invention is a functional fluid composition which comprises ethylene glycol, sodium nitrate, borax, and water, and an effective amount of perfluorinated gem-diphosphonate(s) as a corrosion inhibitor. In another embodiment of the invention, one or more perfluorinated compounds are included in an antifreeze formulation comprising ethylene glycol and dipotassium phosphate and water. The invention also provides for the above compositions which are undiluted, that is, without added water.

The method of inhibiting metal corrosion according to the invention will comprise adding an effective amount of one or more perfluorinated gem-diphosphonate compounds to a functional fluid composition, such as for example, antifreeze.

DETAILED DESCRIPTION OF THE PREFERRED EMBODIMENTS

Figure 1:
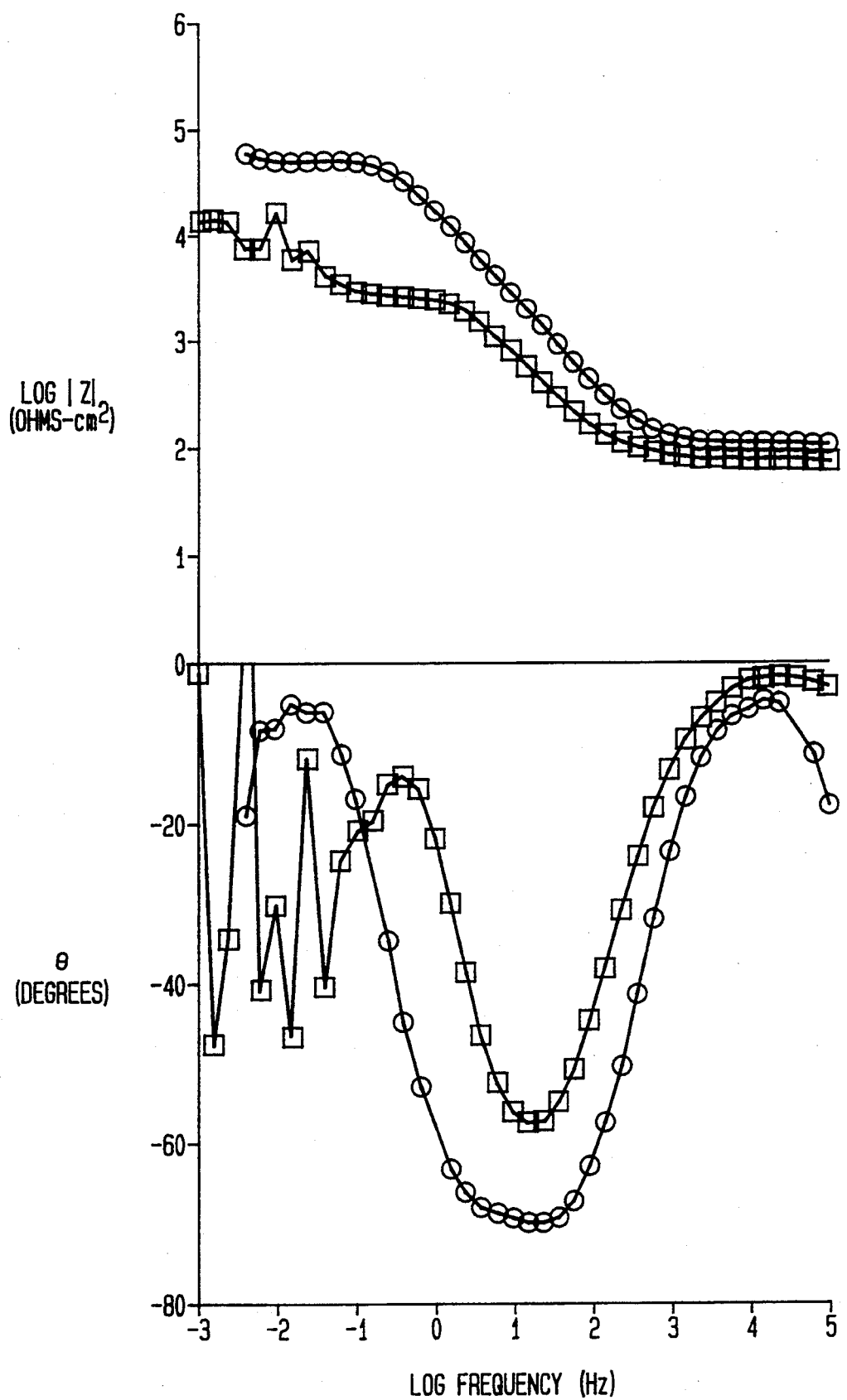
FIG. 1 is a Bode alpha plot for a known antifreeze composition v. antifreeze formulation according to one embodiment of the invention.

Perfluorinated gem-diphosphonate compounds have now been found to be extremely useful in inhibiting corrosion.

Perfluoro-gem-diphosphonates may be synthesized with some guidance from Germscheid, U.S. Pat. No. 3,855,284, which addresses the formation of phosphonates from alkyl carboxylic acids. It has now been discovered that when perfluoro-alkyl carboxylic acids are reacted with $PCl_3$ and water, the following reaction occurs:

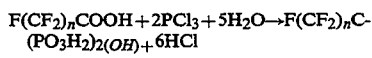

The compositions according to the various embodiments of the invention will contain perfluorinated compounds having the above formula wherein n equals about 1 to 7. When n=1, for example, the product is perfluoro-1-hydroxyethylidene-1,1-diphosphonic acid, or PF-HEDPA. The n=3 sample will be the product perfluoro-1-hydroxybutylidene-1,1-diphosphonic acid (PF-HBDPA). When n=6, the product is perfluoro-1-hydroxyheptylidene-1,1-diphosphonic acid (PF-HHDPA). The n=7 sample will yield the product perfluoro-1-hydroxyoctylidene-1,1-diphosphonic acid, or PF-HODPA, and so on. The perfluorinated compounds according to the invention will have the following structural formula:

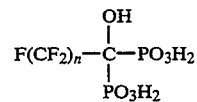

wherein n equals about 1 to 7.

Especially preferred are the perfluorinated gem-diphosphonates of the above formula wherein n equals about 3 to 6, and even preferably about 6.

When the perfluorinated gem-diphosphonates of the invention are added to functional fluid compositions, especially antifreeze, these compounds have shown excellent utility in inhibiting corrosion and buildups on aluminum. Those skilled in the art will also recognize that other metals and alloys requiring corrosion protection are also within the scope of the invention. It is also expected that the these compounds will find utility in antiicing and antifriction applications as well.

The term "coolant" or "antifreeze" composition is used interchangeably herein, and as a subset of functional fluid compositions refers to those formulations which are typically added to engine radiators and internal combustion engines and other fluid systems to maintain operating temperatures at safe levels, and to prevent overheating and subsequent breakdown.

The corrosion inhibitors which are perfluoro analogs of the gem-diphosphonates of the present invention are preferably utilized in those coolant compositions for use in automotive vehicle radiators which comprise as their major component one or more glycols or glycol ethers. The glycol or glycol ethers that can be used in coolants include ethylene glycol, diethylene glycol, propylene glycol, dipropylene glycol, the methyl, ethyl, propyl or butyl ethers of these glycols, and the methyl and ethyl diethers of ethylene glycol, diethylene glycol, or dipropylene glycol, as well as mixtures thereof.

A typical formulation may comprise about 40–70%, preferably about 40–60%, and most preferably about 50% of one or more of the aforementioned glycol or glycol ethers, in combination with water, or water and one or more additives (hereinafter described). Especially preferred for use with the present invention is the coolant ethylene glycol, either alone (undiluted) or more preferably, in combination with water. (Unless otherwise stated, all percentages expressed herein are set forth in terms of weight based upon the total weight of the composition.)

The perfluoro- gem-diphosphonates may be added to any of the glycol or glycol ether formulations in amounts of from about 0.05–1%, preferably from about 0.05–0.5%, and more preferably from about 0.1 to 0.5%. One especially desirable formulation may comprise one or more of the aforementioned glycols or glycol ethers (without water dilution), especially ethylene glycol, in combination with one or more perfluorinated gem-diphosphonates in amounts of from about 0.05–1.0%, and especially about 0.1–0.4%.

The coolant formulations of the present invention may also comprise one or more additional coolant additives. These additional additives may be utilized to maintain pH, prevent foaming, dye the coolant, control scale, provide reserve alkalinity, enhance cavitation resistance, enhance corrosion inhibition or modify taste or smell. Two additives which may be found in coolant compositions include sodium nitrate ($NaNO_3$) and borax.$5H_2O$. Sodium nitrate is added to maintain the inner oxide layer of aluminum, while borax is added as a buffer and to provide reserve alkalinity. Typically, sodium nitrate is added in an amount of from about 0.1–1%, preferably about 0.2–0.5%, and most preferably about 0.25%. Borax is utilized in an amount of from about 0.1–1%, preferably from about 0.25–0.75%, and most preferably about 0.5%. Those skilled in the art may find that more of less of the above additives may be utilized.

The pH of the antifreeze formulations according to the various embodiments will range from about 5 to 12, and more preferably from about 5.5 to 9. It is especially desirable that the coolant compositions set forth herein have a pH in the range of about 6.5 to 7.5.

One especially desirable coolant composition will therefore comprise about 40–60% of one or more glycols or glycol ethers, preferably ethylene glycol, with about 0.25% sodium nitrate and about 0.5% borax. To this formulation will be added one or more perfluoro gem-diphosphonates in amounts ranging from about 0.05–1%, preferably from about 0.1–0.5%, with the balance being water. In those formulations without water, there will be the perfluoro gem-diphosphonate(s) in amounts ranging from about 0.1–1.0%, preferably from about 0.2–0.5%, in combination with about 0.25% sodium nitrate and about 0.5% borax, the remainder of the composition being one or more glycols or glycol ethers, especially ethylene glycol.

In another embodiment of the invention, one or more glycols or glycol ethers, especially ethylene glycol, and water together with dipotassium phosphate ($K_2HPO_4$) will comprise a preferred coolant composition to which the perfluor-gem-diphosphonates will be added. This composition will comprise from about 40–70% of one or more glycols or glycol ethers, desirably ethylene glycol, preferably from about 40–60%, and most preferably 50%, in combination with from about 0.1–1% dipotassium phosphate, preferably from about 0.1–0.75%, and most preferably about 0.1 to 0.5%. To any of these compositions will be added from about 0.05–1%, and preferably from 0.1–0.5% of one or more perfluoro- gem-diphosphonates, the balance being water. An especially preferred formulation will therefore comprise about 50% ethylene glycol, about 0.5% dipotassium phosphate, and about 0.1–0.5% of perfluor-gem-diphosphonate(s), the balance being water. There can also be the formulation undiluted containing about 0.5% dipotassium phosphate, about 0.1–1% of perfluoro gem-diphosphonate(s), and the balance being one or more glycols or glycol ethers, more preferably ethylene glycol.

Those skilled in the art may discover that higher or lower concentrations of perfluorinated gem-diphosphonates will work well in the aforementioned compositions. The concentration of these diphosphonates necessary to adequately inhibit corrosion is believed to be dependent on the structure, and the particular alloy, as well as on the medium.

While the main application of the perfluoro-gem-diphosphonates ill be in coolant compositions, it is also expected that these compounds will also be effective in other functional fluids, e.g., hydraulic fluids, metal cutting fluids, boilers, cooling waters, etc. Since these compounds appear to lay down a waxy layer on most metals, they are also promising as lubricants for cutting down frictional wear, for example in the water pump in automobiles, and especially in hydraulic pumps.

The method of inhibiting corrosion on metallic surfaces according to the invention will comprise adding an effective amount of one or more of the perfluoro-gem-diphosphonates to a functional fluid composition, especially a coolant or antifreeze formulation according to the various embodiments heretofore set forth. The coolant composition will in turn be added to a coolant system, for example, an automotive vehicle radiator, as well as to other functional fluid systems, including hydraulic fluid systems.

EXAMPLES

The following examples will help to illustrate the invention, but in no way should be construed as limiting the scope thereof:

Electrochemical Testing

The screening tests were carried out in BAF2 at 82.2° C. BAF2 contained 50% distilled water, 49.75% antifreeze grade ethylene glycol containing 5 to 8% diethylene glycol, 0.25% sodium nitrate and 0.5% borax.5hydrate. Varying amounts of the corrosion inhibitors according to the invention were added to BAF2, as set forth in the Examples.

Keithley Model 616 and 614 digital electrometers were used to measure the corrosion potentials which were recorded on a two channel Houston Instrument recorder. For EIS (electrochemical impedance spectroscopy), a combination of a Solartron 1255 frequency response analyzer/EG&G PARC Model 273 Potentiostat galvanostat/EG & G PARC Model 388 software was used for conducting the experiments as well as analyzing and plotting the data.

The test cell consisted of a 500 mL flat-bottomed beaker as described in reference 5 with the exception that silver/silver polysulfide reference electrode was substituted for the SCE (saturated calomel electrode). The working electrode was 3003-14 (UNS A93003) aluminum in sheet forms whereas the counter electrode was a pair of ultrafine graphite rods. Aluminum discs having diameters of 1.5 cm were cut and prepared according to ASTM practice G-1 using 600 grit diamond slurry on a flat lapping machine by Metals Samples and used as is. The specimens were mounted in flat specimen holders.

The solutions were prepared in the cell which was then attached to the cell cover. The cell cover had provisions for the electrodes and a thermocouple. Recording of $E_{corr}$ was started after the positive lead of the electrometer was connected to the working electrode, and the negative lead was connected to the reference electrode. The solution was continually stirred and heated until the solution temperature stabilized in about fifteen minutes at 82.2° C. (180° F.), thereby simulating the temperature of an automotive cooling system. After another fifteen minutes, the stirrer was turned off and the EI spectrum was measured five hours later.

The corrosion rate $i_{corr}$ can be determined using the following equations:

$$R_p = B/i_{corr}$$

$$B = b_a b_c / 2.3(b_a + b_c)$$

The $R_p$ obtained from EIS data is seen to be inversely proportional to the corrosion rate, i.e., the higher the $R_p$, the lower the corrosion rate. $b_a + b_c$ are the anodic and cathodic Tafel constants, respectively.

For the Bode - alpha plots hereinafter described, the x axis denotes log frequency in hertz (Hz). The upper plot on the y axis represents log impedance (log z) in ohm-cm$^2$. The lower plot on the y axis represents the Greek theta, or the phase angle. The phase angle is the angle between the applied voltage and current response for a particular sample. There are two limiting cases: theta is zero degrees for a pure resistor, and is $-90$ degrees for a pure capacitor. $R_p$ can be estimated from the value of log impedance at the origin. This is a slight simplification and ignores a very small, common factor.

Example 1

FIG. 1 shows the Bode alpha plots for BAF2 (squares) and BAF2 containing 500 ppm PF-HBDPA (perfluoro-1-hydroxybutylidene-1,1-diphosphonic acid (circles) at 180° C. and pH=7.48. One and a half decades rise in log /z/ indicates that the corrosion rate has been decreased about 50× and the decrease in noise indicate that the protective film has been stabilized by PF-HBDPA.

Example 2

Figure 2:
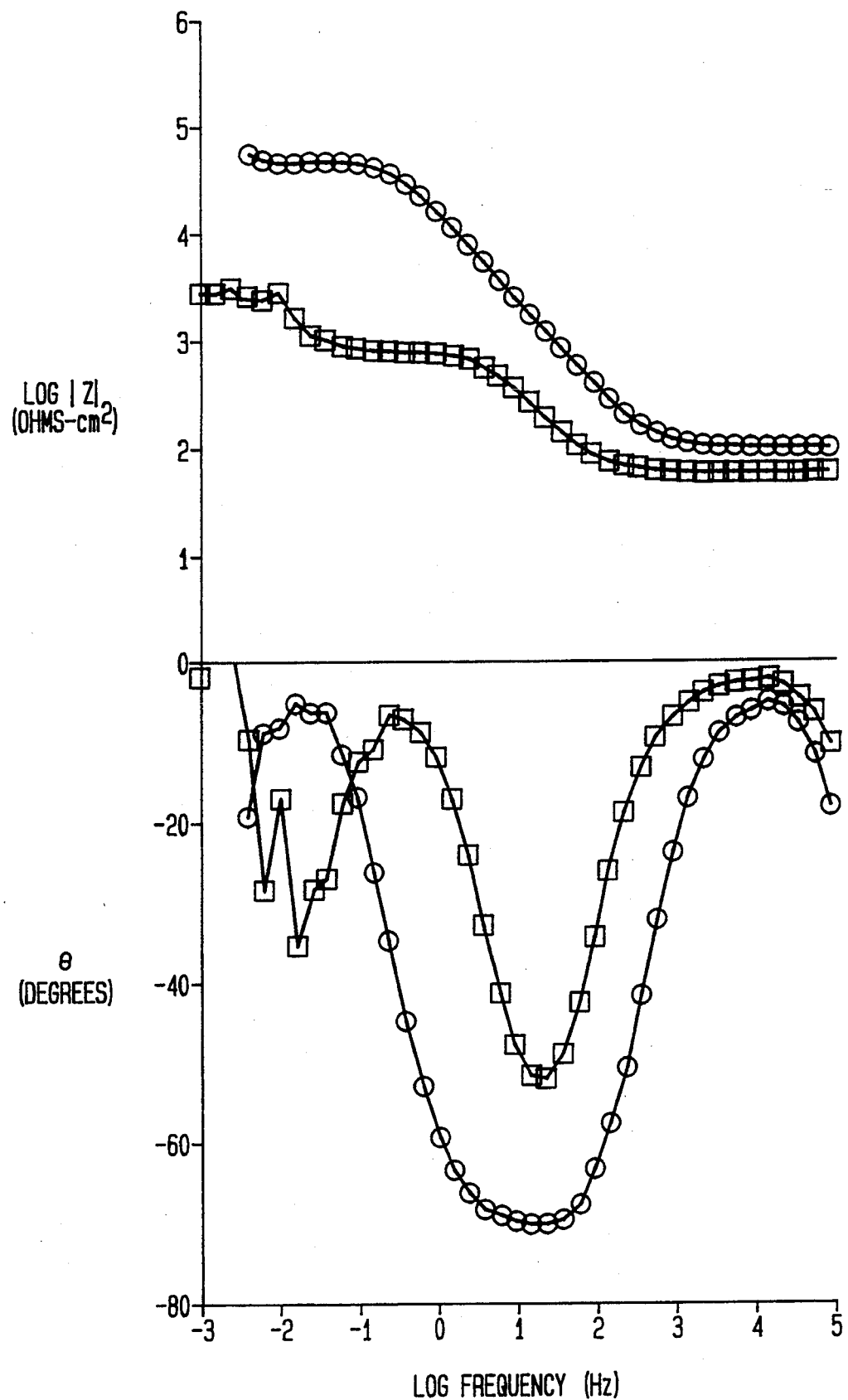
FIG. 2 is a Bode alpha plot for another known antifreeze formulation v. the novel antifreeze composition of FIG. 1.

FIG. 2 compares the Bode alpha plots of Al in BAF2 containing either 500 ppm HBDPA (squares) or 500 ppm PF-HBDPA (circles) at 180° C. and pH=8.62. Compared to the gem-diphosphonate, the perfluoro-gem-diphosphonate caused a 100× decrease in the corrosion rate and the noise at low frequencies was decreased which indicated the formation of a stable film.

Examples 3 and 4

Figure 3:
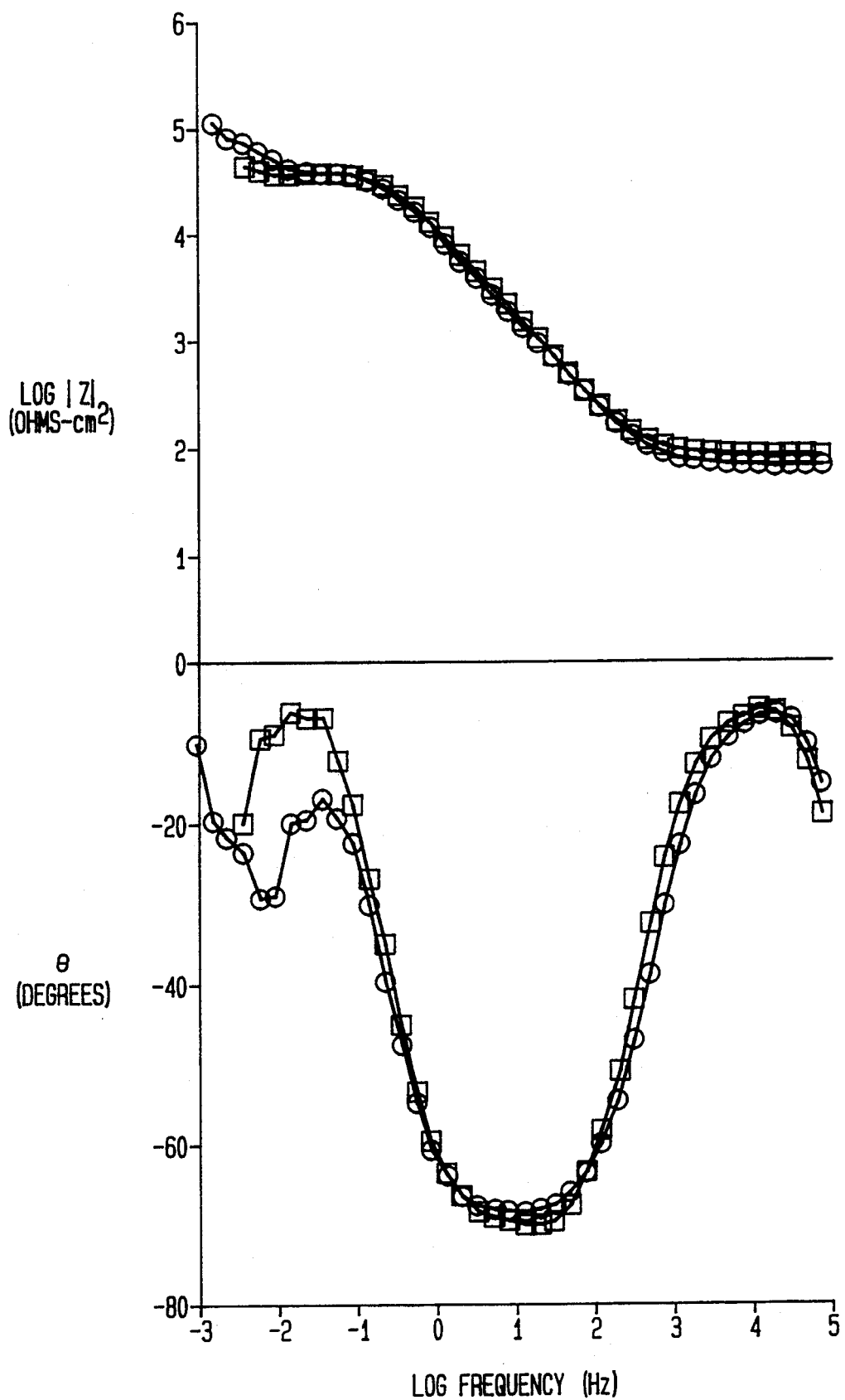
FIG. 3 is a Bode alpha plot for the novel antifreeze composition of FIG. 1, together with another antifreeze formulation according to an additional embodiment of the invention.
Figure 4:
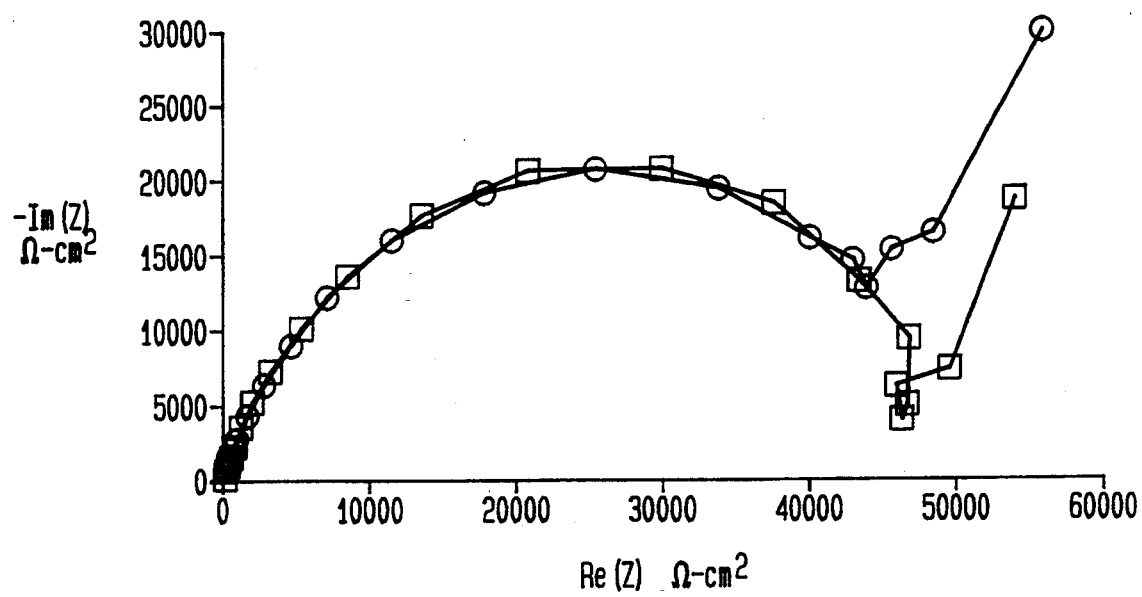
FIG. 4 is a Nyquist plot comparing the novel antifreeze formulations of FIG. 3.

PF-HHDPA (perfluoro-1-hydroxyheptylidene-1,1-diphosphonic acid) (circles) is compared with PF-HBDPA (squares) in the Bode alpha plots in FIG. 3 and the Nyquist plots in FIG. 4 at 0.05% concentration in BAF2 at 180° C. They are equally as effective as corrosion inhibitor for Al.

The experimental procedures, apparatus and data analysis for Examples 1 through 4 above are also outlined in "Use of Electrochemical Noise in the Study of Inhibitor Systems for Aluminum" by S. T. Hirozawa and D. E. Turcotte in *Materials Performance Maintenance—Proceedings of the International Symposium*, pp. 207–222, Pergammon Press, N.Y. (1991).

While the invention has been described in each of its embodiments, it is to be understood that certain modifications may occur to those skilled in the art without departing from the true spirit and scope of the invention as set forth in the specification and the accompanying claims.

What is claimed is:

1. A functional fluid composition effective in inhibiting metal corrosion, comprising from about 40 to 70% of one or more glycols and glycol ethers and from about 0.05 to 1% of at least one perfluoro-gem-diphosphonate having the following formula:

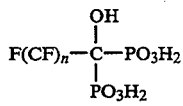

wherein n=about 1 to 7.

2. A method of inhibiting aluminum corrosion in coolant systems which comprises adding thereto from about 0.05 to 1% of one or more perfluoro-gem-diphosphonates having the following formula:

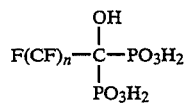

wherein n=about 1 to 7.

3. A coolant or antifreeze composition effective in inhibiting metal corrosion, comprising one or more glycols and glycols ethers and from about 0.1–1.0% of one or more perfluoro-gem-diphosphonates having the following formula:

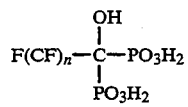

wherein, n=from about 1 to 7.

4. A perfluorinated gem-diphosphonate compound of the following formula:

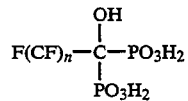

wherein n=about 1 to 7, said compound being useful in inhibiting corrosion on metals.

5. The composition as claimed in claim 1, wherein the value of n is from about 3 to 6.

6. The composition as claimed in claim 5, comprising from about 40 to 60% of one or more glycol or glycol ethers.

7. The composition as claimed in claim 6, wherein said glycol ether is ethylene glycol.

8. The composition as claimed in claim 6, comprising from about 0.05 to 0.5% of said perfluoro-gem-diphosphonates.

9. The composition as claimed in claim 8, comprising from about 0.1 to 0.5% of said perfluoro-gem-diphosphonates.

10. The composition as claimed in claim 9, comprising about 50% of said ethylene glycol, and further comprising from about 0.1 to 1% of at least one additive selected from the group consisting of dipotassium phosphate, sodium nitrate and borax.5H$_2$O.

11. The composition as claimed in claim 10, further comprising water.

12. The composition as claimed in claim 9, wherein said composition has a pH within the range of about 5.5 to 9.

13. The composition as claimed in claim 12, wherein said composition has a pH within the range of about 6.5 to 7.5.

14. The composition as claimed in claim 12, wherein the value of n is about 6.

15. The compound as claimed in claim 4, wherein value of n is from about 3 to 6.

16. The compound as claimed in claim 15, wherein the value of n is about 6.

* * * * *